(12) United States Patent
Samsoondar

(10) Patent No.: US 7,638,342 B2
(45) Date of Patent: Dec. 29, 2009

(54) SPECTROPHOTOMETRIC ANALYSIS OF PLASMA IN A CLOSED-CONTAINER

(75) Inventor: James Samsoondar, Cambridge (CA)

(73) Assignee: NIResults Inc., Toronto, Ontario (CA)

(*) Notice: Subject to any disclaimer, the term of this patent is extended or adjusted under 35 U.S.C. 154(b) by 39 days.

(21) Appl. No.: 10/590,431

(22) PCT Filed: Feb. 24, 2005

(86) PCT No.: PCT/CA2005/000269

§ 371 (c)(1),
(2), (4) Date: Aug. 22, 2007

(87) PCT Pub. No.: WO2005/080965

PCT Pub. Date: Sep. 1, 2005

(65) Prior Publication Data

US 2008/0096282 A1 Apr. 24, 2008

(30) Foreign Application Priority Data

Feb. 24, 2004 (CA) .................................... 2458497

(51) Int. Cl.
*G01N 1/18* (2006.01)
*G01N 33/48* (2006.01)
*G01N 33/49* (2006.01)
*G01N 1/28* (2006.01)
*G01N 21/07* (2006.01)
*G01N 21/25* (2006.01)

(52) U.S. Cl. .......................... 436/177; 436/45; 436/63; 436/164; 436/165; 436/171; 436/174

(58) Field of Classification Search .................. 436/45, 436/63, 164, 165, 171, 174, 177; 422/72, 422/82.05, 82.09, 101
See application file for complete search history.

(56) References Cited

U.S. PATENT DOCUMENTS 3,761,408 A * 9/1973 Lee ............................ 210/782
3,951,801 A    4/1976 Ayres
4,119,407 A * 10/1978 Goldstein et al. ............. 422/58
6,706,536 B1 * 3/2004 Carroll et al. ................ 436/164

FOREIGN PATENT DOCUMENTS

EP    0 001 200 A1    3/1979

OTHER PUBLICATIONS

Copeland, B.E., M.D., et al., "Hemoglobin by First Derivative Spectrophotometry: Extent of Hemolysis...," Annals of Clinical and Laboratory Science 9:383-388(1969).

* cited by examiner

Primary Examiner—Maureen M Wallenhorst
(74) Attorney, Agent, or Firm—Quarles & Brady LLP

(57) ABSTRACT

The present invention provides a method of analyzing plasma from a sample of whole blood. The method includes a) obtaining a sample of whole blood from a subject in a container, the container having a first end and a second end, the first end of the container for receiving a sample of whole blood; b) centrifuging the container under conditions to separate the whole blood into a cell layer, a gel layer and a plasma layer, wherein the centrifuging produces in relative juxtaposition the first end of the container, the cell layer, the gel layer, the plasma layer and the second end of the container; and c) inserting into a spectrophotometric device the second end of the container which includes the plasma layer in closest relative juxtaposition, to analyze the plasma from the whole blood.

16 Claims, 2 Drawing Sheets

SPECTROPHOTOMETRIC ANALYSIS OF PLASMA IN A CLOSED-CONTAINER

FIELD OF INVENTION

The present invention relates to methods for assaying plasma from whole blood samples.

BACKGROUND OF THE INVENTION

A variety of containers and tubes are known in the art for collecting blood samples. Further, a variety of containers, for example Vacutainer® (Becton Dickinson) and methods are known in the art for centrifuging and separating whole blood into component layers including a cell layer, a gel layer and a plasma layer. However, a major drawback with the prior art methods is that the containers must be opened in order to analyze the plasma contained therein, thereby increasing the risk of infecting personnel with agents contained in the blood, and also increasing the risk of contaminating the blood during sampling. Thus, there is a need in the art for methods to analyze blood samples wherein the containers need not be opened to analyze plasma. Further, direct assaying of plasma following centrifugation is complicated by varied sample volumes that preclude direct assaying using a spectrophotometer. Also, direct assay of the plasma layer is often complicated due to the location of labels on the collection tubes, which may overlap the plasma layer. Thus, there is a need to overcome drawbacks in the art.

It is an object of the present invention to overcome drawbacks in the prior art.

The above object is met by a combination of the features of the main claims. The sub claims disclose further advantageous embodiments of the invention.

SUMMARY OF THE INVENTION

The present invention relates to methods for assaying plasma from whole blood samples.

According to the present invention there is provided a method of analyzing plasma from a sample of whole blood comprising,
   a) obtaining a sample of whole blood from a subject in a container, the container comprising a first end and a second end, the first end of the container for receiving a sample of whole blood;
   b) centrifuging the container under conditions to separate the whole blood into a cell layer, a gel layer and a plasma layer, wherein the centrifuging produces in order: the first end of the container, the cell layer, the gel layer, the plasma layer and the second end of the container;
   c) inserting into a spectrophotometric device the second end of the container which comprises the plasma layer in closest relative position, to analyze the plasma from the whole blood.

The present invention further contemplates the method as defined above wherein the container comprises a Vacutainer or a similar receptacle for collecting blood from a subject.

The present invention also provides a method as recited above wherein the container comprises a septum, preferably a rubber septum at the first end.

The present invention also provides a method as defined above wherein the sample of whole blood comprises from about 1 ml to about 10 ml in the container.

The present invention also provides a method as defined above wherein the step of centrifuging comprises centrifuging the sample at about 1000×g. Preferably the sample is centrifuged for between about 5 to about 10 minutes. It is also contemplated that the centrifuging may be performed under refrigerated conditions, for example, but not limited to a temperature from about 0° C. to about 20°C.

The present invention also provides a method as defined above wherein the container is of a shape and the whole blood sample is of a volume such that the step of centrifuging provides a plasma layer of at least 3 mm or more when the container is vertical. Also, the container may comprise one or more cylindrical, conical, frustoconical, oval, or rectangular shapes, or a combination thereof. It is also contemplated that the container may be substantially flat-bottomed at the first end, the second end, or both.

The present invention also provides a method as defined above wherein the step of centrifuging is performed in a fixed angle rotor or a swing arm rotor.

The present invention also provides a method for analyzing plasma from a sample of whole blood comprising,
   a) obtaining a sample of whole blood from a subject in a vacutainer, the vacutainer comprising a first end and a second end, the first end comprising a rubber septum for receiving a sample of whole blood;
   b) centrifuging the Vacutainer under conditions to separate the whole blood into a cell layer, a gel layer and a plasma layer, wherein the centrifuging produces in relative juxtaposition the first end of the vacutainer, the cell layer, the gel layer, the plasma layer and the second end of the container;
   c) inserting into a spectrophotometric device the second end of the vacutainer which comprises in closest juxtaposition, the plasma layer to analyze the plasma.

The present invention also provides a method for centrifuging a blood sample comprising,
   a) obtaining a sample of whole blood from a subject in a container, the container comprising a first end and a second end, the first end of the container for receiving a sample of whole blood;
   b) centrifuging the container under conditions to separate the whole blood into a cell layer, a gel layer and a plasma layer wherein the centrifuging produces in relative juxtaposition the first end of the container, the cell layer, the gel layer, the plasma layer and the second end of the container.

The present invention also provides a method for centrifuging a blood sample comprising,
   a) obtaining a sample of whole blood from a subject in a vacutainer, the vacutainer comprising a first end and a second end, the first end comprising a septum permitting the vacutainer to receive a sample of whole blood;
   b) centrifuging the vacutainer under conditions to separate the whole blood into a cell layer, a gel layer and a plasma layer wherein the centrifuging produces in relative juxtaposition the first end of the container, the cell layer, the gel layer, the plasma layer and the second end of the container.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
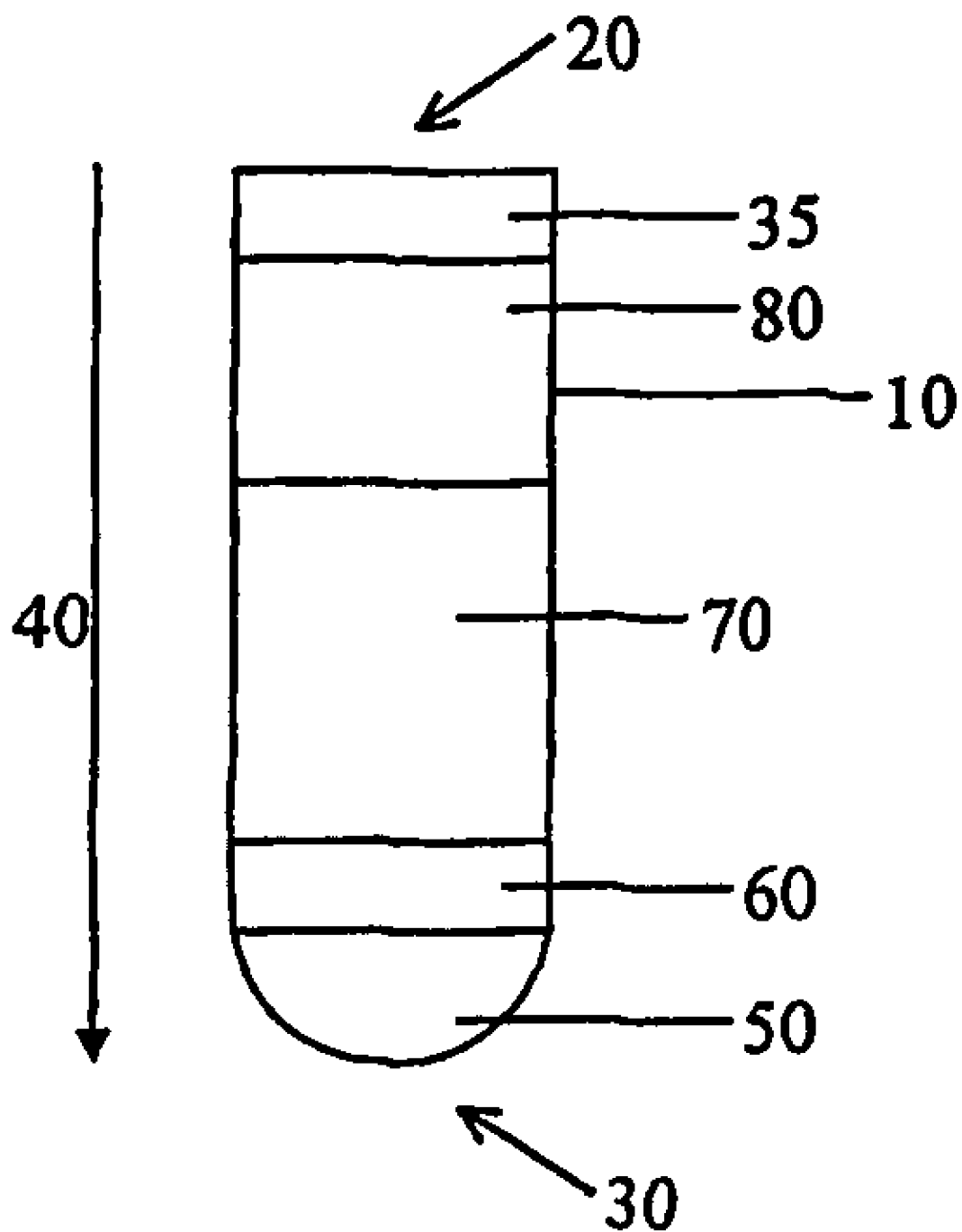
FIG. 1 shows a representative illustration of a whole blood sample following a centrifugation step as known in the prior art.

The following description is of a preferred embodiment.

According to an embodiment of the present invention, there is provided a method of analyzing plasma or serum from a sample of whole blood comprising, a) obtaining a sample of whole blood from a subject in a container, the container comprising a first end and a second end, the first end of the container for receiving a sample of whole blood;

b) centrifuging the container under conditions to separate the whole blood into a cell layer, a gel layer and a plasma layer, wherein the centrifuging produces in relative juxtaposition the first end of the container, the cell layer, the gel layer, the plasma layer and the second end of the container;

c) inserting into a spectrophotometric device the second end of the container which comprises the plasma layer in closest relative juxtaposition, to analyze the plasma from the whole blood.

The container of the present invention may comprise any blood collection container known in the art. Preferably, the blood collection container comprises a material that is substantially transparent to one or more wavelengths that are to be used to analyze the sample in the spectrophotometric device. Examples of such materials include, but are not limited to glass, transparent plastic or translucent plastic. Also, the blood collection container may comprise any shape known in the art, for example, but not limited to cylindrical, conical, frustoconical, oval, or rectangular shapes, or a combination thereof. Preferably, the blood collection container is of a shape that is compatible for use in a spectrophotometric device.

In an embodiment of the present invention, which is not meant to be limiting in any manner, the container may comprise a first end for receiving blood from a subject, the first end comprising a septum, for example, but not limited to a rubber septum. It is also contemplated that the septum may comprise other materials as would be known to a person of skill in the art. It is also contemplated that the container may comprise a screw cap or other similar closure that may be removed from a container to allow blood to be placed therein. An example of the container is a Vacutainer® available from Becton Dickinson.

In a preferred embodiment of the present invention, which is not meant to be limiting in any manner, the container is capable of holding from about 1 ml to about 10 ml of whole blood and is preferably shaped such that after the step of centrifuging there is provided a plasma layer of at least 3 mm or more when the container is vertical. More preferably, the plasma layer is at least 1 cm or more, still more preferably more than about 2 cm, more preferably more than about 4 cm. Without wishing to be limiting or bound by theory, a larger plasma layer may be more easily analyzed in a spectrophotometric device, especially those that are adapted to accept containers that may hold samples of relatively large volumes, for example, but not limited to from about 0.5 ml to about 4 ml. Further, the second end of the container may be curved as in the case of a Vacutainer, or alternatively, the second end may be substantially flat-bottomed to facilitate measurements in the spectrophotometric device.

The cell layer resulting from the step of centrifuging comprises red blood cells (rbc) and preferably amounts to about 40% by volume of the whole blood sample, with plasma making up about 60% by volume of the sample.

The step of centrifuging preferably comprises centrifuging the sample at about 1000×g (gravity), preferably for about 5 to about 10 minutes. However, the centrifugation step may comprise centrifuging under higher forces of gravity and for different times, as would be understood by a person of skill in the art. For example, it may be possible to produce similar centrifugation results by centrifuging the sample under a higher forces of gravity for a shorter time as would be obtained by centrifuging the sample under lower forces of gravity for a longer period of time.

It is also contemplated that the step of centrifuging may be performed at a variety of temperatures, for example, but not limited to the normal physiological temperature of the subject, for example, but not limited at about 37° C. in the case of a human subject. Alternatively, the step of centrifuging may be performed under temperatures less than the normal physiological temperature of the subject, in the range of about 0° C. to about 37° C., or an amount therebetween. In alternate embodiments, which are not meant to be limiting in any manner, the step of centrifuging may be performed at a temperature between about 0° C. to about 20° C., 2° C. to about 15° C., or, in an alternate embodiment, about 1° C. to about 5° C. However, as would be understood by a person of skill in the art, the force of the centrifugation step, the time of the centrifugation step or both may be affected by the temperature of the blood sample as a lower temperature may increase the viscosity of the blood sample. Correcting for differences in the viscosity of the blood as a result of temperature is easily within ability of a person of skill in the art.

The step of centrifuging may be performed in either a fixed-angle rotor or a swing arm rotor.

Any spectrophotometric device known in the art that may be employed to analyze blood plasma may be employed in the method of the present invention. For example but not to be considered limiting in any manner, the spectrophotometric device may be capable of performing measurements, such as, but not limited to absorption, reflectance, transmittance or a combination thereof in the far infrared, near infrared, visible, ultraviolet range or any combination thereof. In a preferred embodiment, the spectrophotometric device is capable of performing measurements in the wavelength range of about 500 nm to about 3000 nm, or any range therebetween.

Referring now to FIG. 1 there is diagrammatically shown the result of a prior art centrifugation step wherein a container (10) comprising whole blood that has been centrifuged according to a typical prior art method. The container (10) as generally shown comprises a first end (20) and a second end (30), the first end comprising a septum (35) that permits blood to be collected into the container (10). Following the centrifugation step and wherein first arrow (40) shows an example of the direction of gravitational force produced by the centrifugation step, the blood sample separates into a cell layer (50), a gel layer (60) and a plasma layer (70) as shown in FIG. 1A.

An air space may also be present (80). In relative juxtaposition the container comprises a first end (20), septum (35), plasma layer (70), gel layer (60), cell layer (50) and second end (30). According to the prior art process, the plasma layer may not be analyzed directly, for example by spectrophotometric analysis without removing a sample of the plasma layer from the container.

Figure 2A:
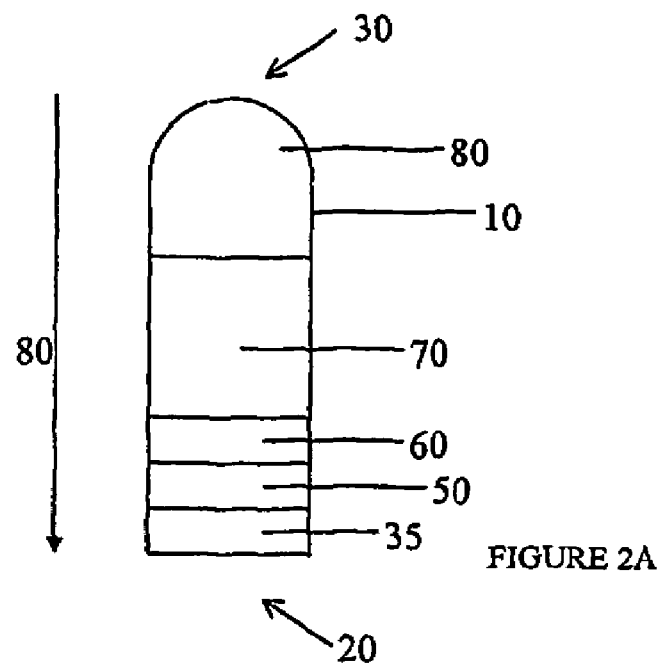
FIG. 2A shows a representative illustration of a whole blood sample following the method of the present invention.
Figure 2B:
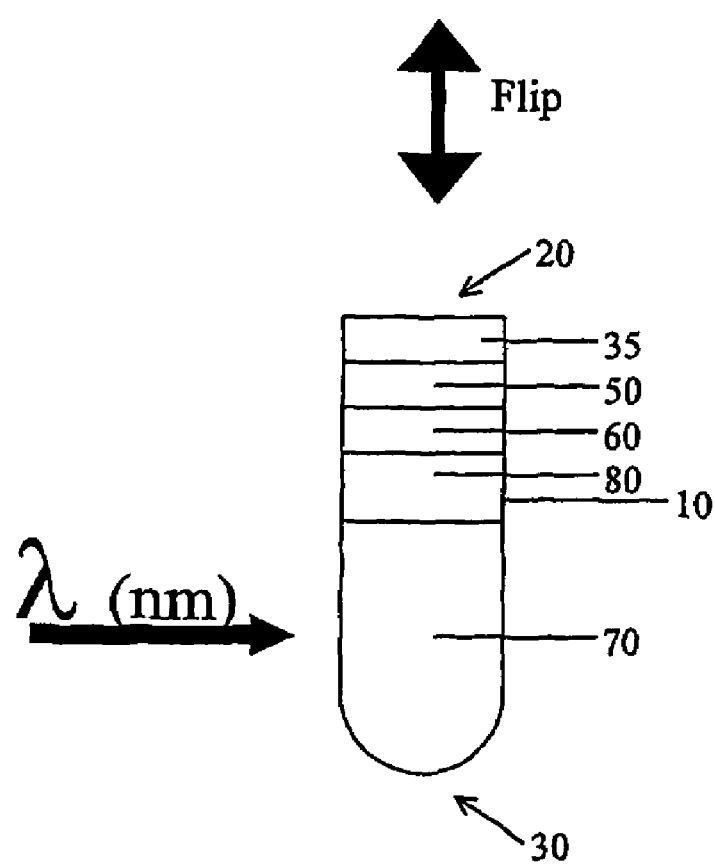
FIG. 2B shows the inverted container of FIG. 2A that may be employed in the analysis of blood plasma.

Referring now to FIGS. 2A and FIG. 2B and without wishing to be limiting in any manner, there is diagramatically shown an embodiment of the present invention, wherein a container (10) of whole blood is centrifuged according to the method of the present invention, and in the direction of gravitational force as shown by the second arrow (80) to produce a container (10) as generally shown that comprises in juxtaposition a first end (20), septum (35), cell layer (50), gel layer (60), plasma layer (70) and second end (30), an air space (80) may also be present. Following centrifugation, the container may be inverted as shown by inversion arrow (FLIP) such that plasma layer (70) falls to second end (30) while the cell layer (50) and gel layer (60) remain stationary. This permits the container (10) to be inserted within a spectrophotometric device for analysis without removing any of the plasma layer from the container.

As will be evident to someone of skill in the art, it is preferable that the container is not shaken, or subjected to forces that could substantially disturb the cell layers and/or the gel layer that are formed by the centrifugation step of the method of the present invention.

In an alternate embodiment of the present invention, which is not meant to be limiting in any manner, there is provided a method for analyzing plasma, or serum (for example, after blood is allowed to clot) from a sample of whole blood comprising, a) obtaining a sample of whole blood from a subject in a vacutainer, the vacutainer comprising a first end and a second end, the first end comprising a rubber septum for receiving a sample of whole blood;
b) centrifuging the Vacutainer under conditions to separate the whole blood into a cell layer, a gel layer and a plasma layer, wherein the centrifuging produces in relative juxtaposition the first end of the vacutainer, the cell layer, the gel layer, the plasma layer and the second end of the container;
c) inserting into a spectrophotometric device the second end of the vacutainer which comprises in closest juxtaposition, the plasma layer to analyze the plasma.

Also contemplated by the present invention, there is provided a method of centrifuging a blood sample comprising, a) obtaining a sample of whole blood from a subject in a container, the container comprising a first end and a second end, the first end of the container for receiving a sample of whole blood;
b) centrifuging the container under conditions to separate the whole blood into a cell layer, a gel layer and a plasma layer wherein the centrifuging produces in relative juxtaposition the first end of the container, the cell layer, the gel layer, the plasma layer and the second end of the container.

In an alternate embodiment of the present invention, which is not meant to be limiting there is provided a method of centrifuging a blood sample comprising, a) obtaining a sample of whole blood from a subject in a vacutainer, the vacutainer comprising a first end and a second end, the first end comprising a septum permitting the vacutainer to receive a sample of whole blood;
b) centrifuging the vacutainer under conditions to separate the whole blood into a cell layer, a gel layer and a plasma layer wherein the centrifuging produces in relative juxtaposition the first end of the container, the cell layer, the gel layer, the plasma layer and the second end of the container.

The present invention contemplates placing the first end of the container at the bottom of a centrifuge tube or rotor and centrifuging the blood sample as described above. In this manner, the step of centrifuging results in a container comprising in order: 1) the first end of the container; 2) the septum, plug, cap, for example, but not limited to the screw cap of the container; 3) a cell layer Comprising red blood cells; 4) a gel layer 5) a plasma layer and 6) the second end of the container.

As will be evident to a person of skill in the art, air may exist between the plasma layer and the second end of the container. In this manner, it is possible take measurements of the plasma layer for example, by inverting the tube such that the plasma layer falls against the second end of the container and inserting the tube (second end down) into a spectrophotometric device to analyze the plasma layer. Also in this way, a label or other sticker which is affixed to the container at about the midportion of the container will not interfere with the analysis of the plasma layer as it does not obstruct the light path employed by the spectrophotometric device.

It is also contemplated that the method of the present invention may further comprise a conventional recentrifugation step, for example, centrifuging the sample such that the cell layer comprising red blood cells is reformed at the second end of the tube, as is done in a conventional centrifugation step. For example, but not wishing to be limiting, such a method may be employed if an aliquot of plasma is to be removed from the container.

Without wishing to be considered limiting in any manner, the method of the present invention permits a closed-container (or closed-tube) analysis of plasma or serum from whole blood samples. Further, the method of the present invention reduces the risk of infection to personnel as containers comprising blood sample needs not be opened and sampled in order to perform tests, for example spectrophotometric tests. Further, the method of the present invention may be employed with tubes that have been labeled at about their midsection or higher, and not near the second end of the container thereby reducing spectroscopic problems associated with labeling containers.

The present invention has been described with regard to one or more embodiments. However, it will be apparent to persons skilled in the art that a number of variations and modifications can be made without departing from the scope of the invention as defined in the claims.

What is claimed is:

1. A method of analyzing plasma from a sample of whole blood, comprising:
a) collecting the sample of whole blood from a subject directly into a container, said container comprising a first end and a second end, wherein the whole blood is introduced into the container at the first end and the first end is sealed;
b) centrifuging said container under conditions to separate said whole blood into a cell layer, a gel layer and a plasma layer, wherein said centrifuging produces in relative juxtaposition the first end of the container, the cell layer, the gel layer, the plasma layer and the second end of the container; and
c) inserting into a spectrophotometric device said second end of the container which comprises the plasma layer in closest relative juxtaposition, to analyze the plasma from the whole blood.

2. The method of claim 1, wherein said container comprises a Vacutainer or a similar receptacle for collecting blood from a subject.

3. The method of claim 2, wherein said Vacutainer comprises a septum at the first end.

4. The method of claim 3, wherein the septum comprises a rubber septum.

5. The method of claim 1, wherein said sample of whole blood is present in an amount of from about 1 ml to about 10 ml in said container.

6. The method of claim 5, wherein said step of centrifuging comprise centrifuging said sample at about 1000×g.

7. The method of claim 6, wherein said step of centrifuging comprises centrifuging said sample for between about 5 to about 10 minutes.

8. The method of claim 1, wherein said step of centrifuging is performed under refrigerated conditions.

9. The method of claim 8, wherein said refrigerated conditions comprise a temperature from about 0° C. to about 20° C.

10. The method of claim 1, wherein said container is of a shape and said whole blood sample is of a volume such that said step of centrifuging provides a plasma layer of at least 3 mm or more when said container is vertical.

11. The method of claim 1, wherein said step of centrifuging is performed in a fixed angle rotor or a swing arm rotor.

12. The method of claim 11, wherein said step of centrifuging is performed in a swing arm rotor.

13. The method of claim 1, wherein said container comprise one or more cylindrical, conical, frustoconical, oval, or rectangular shapes, or a combination thereof.

14. The method of claim 1, wherein the second end of the container is substantially flat-bottomed.

15. The method of claim 1, wherein the container is sealed with a septum.

16. the method of claim 15, wherein the septum comprises a rubber septum.

\* \* \* \* \*